United States Patent
Otaki et al.

(10) Patent No.: US 10,295,516 B2
(45) Date of Patent: May 21, 2019

(54) CALIBRATION DEVICE

(71) Applicant: Tatsuno Corporation, Tokyo (JP)

(72) Inventors: Tsutomu Otaki, Tokyo (JP); Norikazu Osawa, Tokyo (JP)

(73) Assignee: Tatsuno Corporation, Tokyo (JP)

( * ) Notice: Subject to any disclaimer, the term of this patent is extended or adjusted under 35 U.S.C. 154(b) by 207 days.

(21) Appl. No.: 15/272,965

(22) Filed: Sep. 22, 2016

(65) Prior Publication Data

US 2017/0089876 A1    Mar. 30, 2017

(51) Int. Cl.
| | |
|---|---|
| *G01F 25/00* | (2006.01) |
| *G01N 33/00* | (2006.01) |
| *G01N 25/66* | (2006.01) |

(52) U.S. Cl.
CPC ......... *G01N 33/0006* (2013.01); *G01N 25/66* (2013.01)

(58) Field of Classification Search
CPC . G01N 33/0006; G01N 25/66; G01F 25/0046
USPC ... 73/1.06, 1.16, 1.33, 1.36, 1.73, 1.74, 149, 73/861, 223–225, 290 R, 291, 296
See application file for complete search history.

(56) References Cited

U.S. PATENT DOCUMENTS

| | | | | |
|---|---|---|---|---|
| 4,838,096 A | * | 6/1989 | Lowe | ........................ B67B 7/42 |
| | | | | 141/94 |
| 5,301,723 A | | 4/1994 | Goode | |
| 6,250,095 B1 | * | 6/2001 | Kametani | ............. F24F 3/1423 |
| | | | | 62/271 |
| 2008/0209916 A1 | | 9/2008 | White | |
| 2011/0118896 A1 | * | 5/2011 | Holloway | .......... G05B 19/0428 |
| | | | | 700/300 |

FOREIGN PATENT DOCUMENTS

CN           102141193       8/2011

OTHER PUBLICATIONS

European Patent Office, European Search Report, dated Apr. 20, 2017, 8 pages, Munich, Germany

* cited by examiner

*Primary Examiner* — Robert R Raevis
(74) *Attorney, Agent, or Firm* — Stetina Brunda Garred and Brucker; Mark B. Garred

(57) ABSTRACT

To provide a calibration device for an apparatus filling a gas such as hydrogen gas and capable of precisely measuring quantity of the gas such as hydrogen gas that are filled at high pressure. A calibration device of the present invention is characterized by including a filling vessel, accommodated in a measurement housing, to the filling vessel a high pressure fuel gas such as hydrogen gas being fed from outside of the measurement housing, and a scale for measuring a weight of a fuel gas fed to the filling vessel, wherein a dry gas pipe for feeding a dry gas is detachably mounted in the measurement housing. Here, the scale preferably measures the weight of the fuel gas fed to the filling vessel together with a weight of the measurement housing.

7 Claims, 3 Drawing Sheets

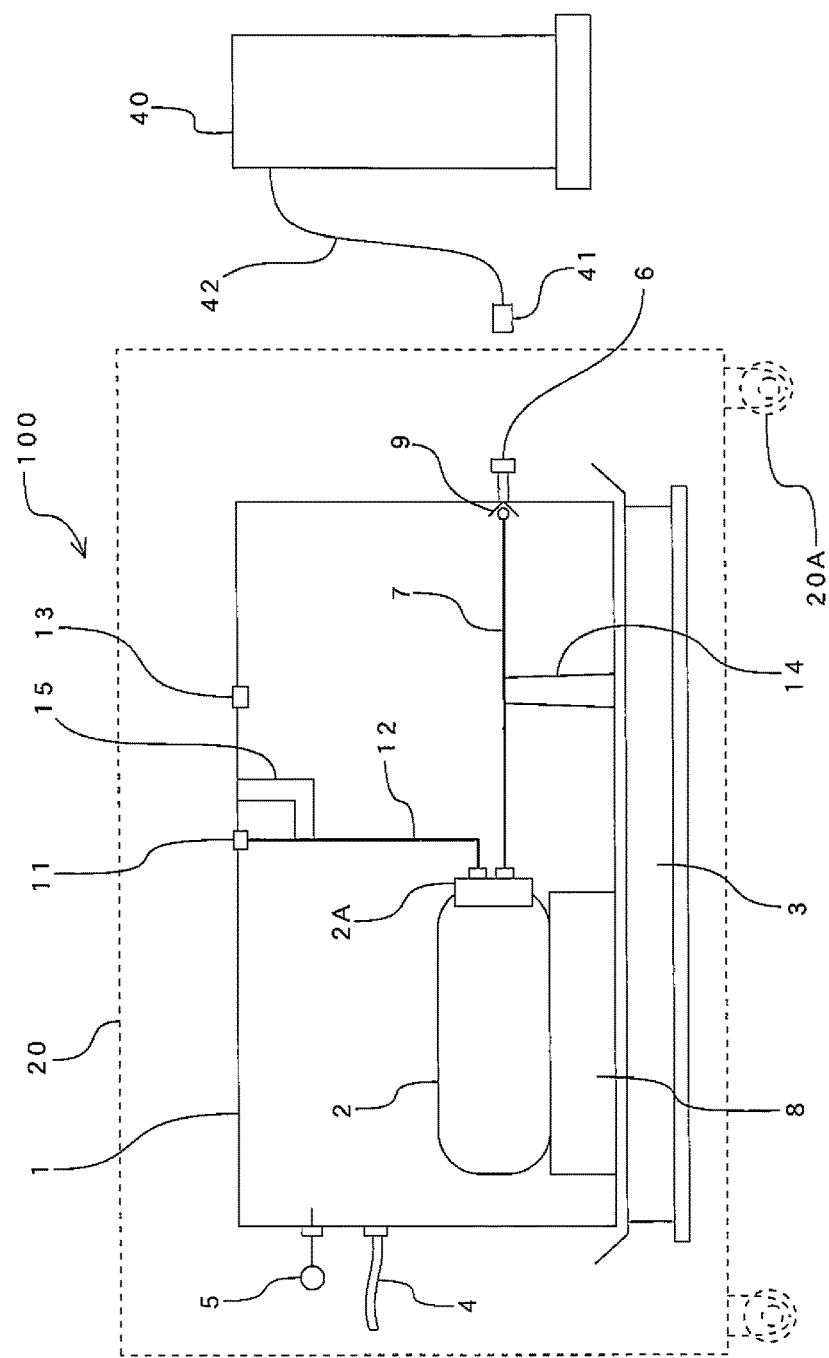
[Fig. 1]

[Fig. 2]
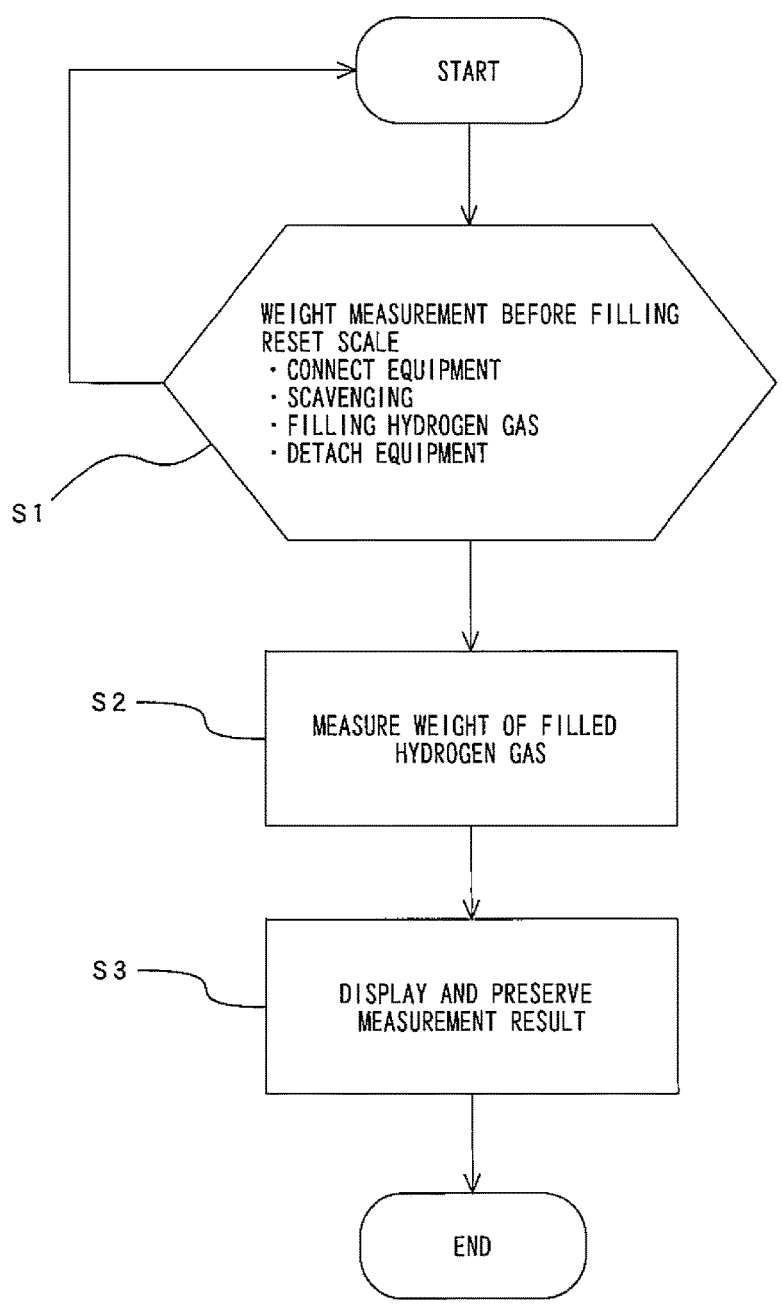

[Fig. 3]
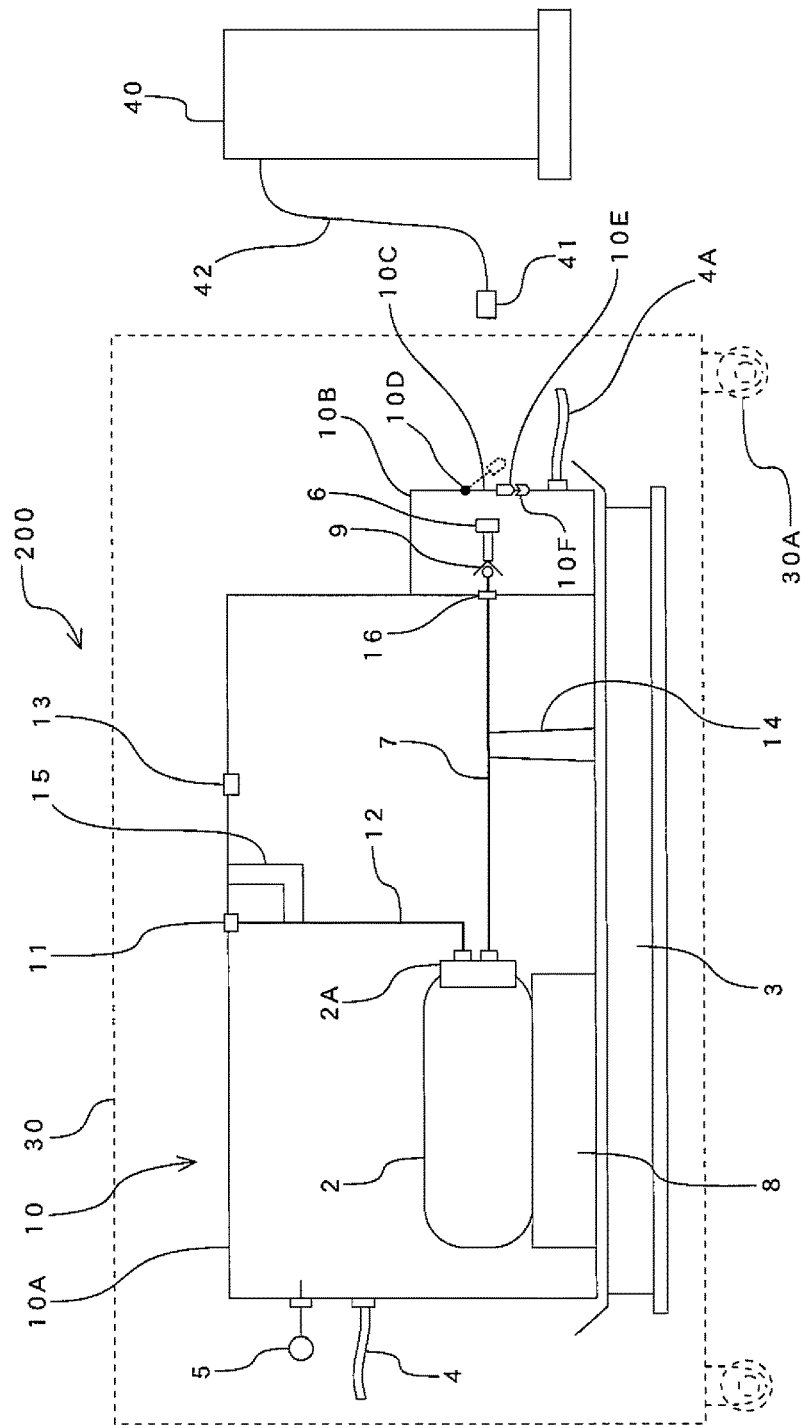

CALIBRATION DEVICE

CROSS-REFERENCE TO RELATED APPLICATIONS

The present application claims priority to Japanese Patent Application No. 2015-189381 filed on Sep. 28, 2015, the disclosure of which is incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates to a calibration device for apparatus filling a gas such as hydrogen gas, and more particularly to a calibration device capable of precisely measuring quantity of a gas such as hydrogen gas filled at high pressure.

2. Description of the Related Art

Gasoline meters installed in filling stations are obliged to take flow rate verification every seven years to maintain fair business dealing, and it is requested that instrumental error of the flow meter is within ±0.5 percent. To such request, the applicant proposes a gasoline meter with inspection mechanism of flow meters in Japanese Patent Publication No. Heisei 07-33197.

In recent years, as a countermeasure for environmental issue, fuel-cell automobiles using hydrogen as fuel have been developed, accordingly hydrogen filling apparatus and calibration devices for the hydrogen filling apparatus have been investigated.

Here in the filling of the hydrogen, high pressure filling is adopted to shorten the filling time, but temperature of the gas increases in association with the high pressure filling, and fuel tanks of fuel-cell vehicles become high in temperature, which may cause breakage of the fuel tanks. In order to prevent the possibility, hydrogen is filled while being cooled at −40° C. with a cooling device.

However, when hydrogen is filled into a calibration device of a hydrogen filling apparatus while being cooled at −40° C., temperatures of a receptacle, a filling gas supply pipe, a filling vessel and other parts become lower than ambient temperature, so that dew condenses on the equipment. When the dew evaporates, weight of overall calibration device changes, resulting in a problem that precise calibration becomes impossible.

In addition, when hydrogen gas is released form the filling vessel of the calibration device, temperature of the filling vessel becomes low due to adiabatic expansion phenomenon to produce water droplets through dew condensation. Then, when several calibrations are performed, due condensations and evaporations repeatedly occur on the large surfaces of the filling vessel, so that weight changes of the calibration device are remarkable, resulting in impossibility of precise measurement.

The contents of Japanese Patent Publication No. Heisei 07-33197 is incorporated herein by reference in its entirety.

SUMMARY OF THE INVENTION

The present invention has been made in consideration of the above problems in the conventional arts, and the object thereof is to provide a calibration device for an apparatus filling a gas such as hydrogen gas and capable of precisely measuring quantity of the gas such as hydrogen gas that are filled at high pressure.

Calibration devices 100, 200 according to the present invention are characterized by including a filling vessel 2, accommodated in measurement housings 1, 10, to the filling vessel 2 a high pressure fuel gas being fed from outside of the measurement housings 1, 10, and a scale 3 for measuring a weight of a fuel gas fed to the filling vessel 2, wherein a dry gas pipe 4 for feeding the dry gas in the measurement housings 1, 10 is detachably mounted to the measurement housings 1, 10. Here, the scale 3 preferably measures the weight of the fuel gas fed to the filling vessel 2 together with a weight of each measurement housing 1, 10.

In the present invention, the measurement housings 1, 10 preferably are semi-enclosed structure. Here, "semi-enclosed structure" means a structure realizing not perfectly sealed state, but nearly sealed state.

In addition, in the present invention, a dew-point instrument 5 for measuring a dew-point temperature in the measurement housings 1, 10 is preferably mounted. The dew-point instrument 5 can be detachably mounted not only on the outside of the measurement housings 1, 10, but also on the inside thereof.

Or, in the present invention, the measurement housing 10 preferably has a first chamber 10A with the filling vessel 2 and a second chamber 10B for accommodating a receptacle 6. In this case, it is preferable that flow rate of the dry gas per unit volume in the second chamber 10B is more than that in the first chamber 10A.

When the present invention is carried out, as the dry gas can be utilized inert gas such as nitrogen, argon and helium, carbon dioxide, and dried air. As the dry gas can be adapted any gases that can be obtained at low cost; easily filled into or discharged from the measurement housings 1, 10 for a short period of time; and has a characteristic contributing to improvement of safety.

With the present invention having the above construction, the dry gas pipe 4 for feeding the dry gas in the measurement housings 1, 10 is mounted, and through the dry gas pipe 4, the dry gas can be filled in the measurement housings 1, 10. And, filling the dry gas in the measurement housings 1, 10 causes air and other gases with moisture to be discharged. As a result, even when a fuel gas such as hydrogen gas that has been cooled at −40° C. is fed to the filling vessel 2 in the calibration devices 100, 200, it is prevented that dew condenses on the equipment in the measurement housings 1, 10. That is, the present invention can prevent dew condensation on the equipment in the measurement housings 1, 10, and can perform a calibration with high accuracy, reliability and safety.

Here, with the present invention, the dry gas pipe 4 is detachably mounted to the measurement housings 1, 10, so that at a weight measurement in the calibration, the dry gas pipe 4 can be separated from the measurement housings 1, 10, which prevents that stresses generating in the members configuring the dry gas pipe 4 vary the results of weight measurement.

With the present invention, since it is prevented that dew condenses on the equipment in the measurement housings 1, 10, it is unnecessary to suspend the weight measurement until a pipe on which dew condenses is dried. Therefore, in case that fuel gas such as hydrogen gas that has been cooled at −40° C. is continuously filled in the filling vessel 2 of the calibration devices 100, 200, it is unnecessary to wait until the equipment on which dew condenses is dried every filling, and the filling can be continuously performed together with the calibration or various tests.

In addition, in the present invention, adopting semi-enclosed structure for the measurement housings 1, 10 and maintaining the measurement housings 1, 10 in slightly pressurized state by the dry gas prevents air with moisture from entering into the measurement housings 1, 10.

And, without the air with moisture entering in the measurement housings 1, 10, hydrogen gas cooled at −40° C. can be filled without dew condensation on the receptacle 6, a filling gas supply pipe 7, the filling vessel 2 and other parts.

Further, in the present invention, mounting a dew-point instrument 5 for measuring dew-point temperatures in the measurement housings 1, 10 prevents the dew condensation by performing adequate humidity management in the measurement housings 1, 10 based on measured results by the dew-point instrument 5. For example, when the dew-point temperature in the measurement housing 1 is a prescribed temperature, which is −20° C. for instance, that is a dew-point temperature that can be judged it is sufficiently dried in the measurement housing 1, and a fuel gas, for example, hydrogen gas that is cooled at −40° C., is fed, amount of dew condensing on the receptacle 6, the filling gas supply pipe 7, the filling vessel 2 and other parts becomes few, so that the amount hardly effects on the weight measurement.

Here, it is expected that decreasing the dew point to −40° C. or less for instance causes the amount of the condensing dew to become zero, but the difference between the amount at −40° C. or less and that at −20° C. or less is small. Therefore, it is realistic and economical that the dew-point temperature is set from −20° C. to −25° C. as a reference dew-point temperature that can be judged to be necessarily and sufficiently dried.

Or, in the present invention, the measurement housing 10 preferably includes the first chamber 10A having the filling vessel 2 and the second chamber 10B accommodating the receptacle 6. With this, when the filling nozzle 41 of an apparatus to be calibrated, which is the hydrogen filling apparatus 40 for instance, is detached from the receptacle 6, dew condenses on the equipment accommodated in the second chamber 10B only, and it can be prevented that dew condenses on the equipment accommodated in the first chamber 10A. Therefore, amount of dew condensing on overall calibration device 200 decreases, which suppresses reduction in detection accuracy due to dew condensation.

In this case, into the second chamber 10B enters air with moisture every time the filling nozzle 41 is detached from the receptacle 6, but it is unlikely that air with moisture enters into the first chamber 10A, so that it is preferable that flow rate of the dry gas per unit volume in the second chamber 10B is more than that in the first chamber 10A. In addition, it is preferable that the flow rates can be adjusted separately.

BRIEF DESCRIPTION OF THE DRAWINGS

FIG. 1 is a block diagram showing the first embodiment of the present invention;

FIG. 2 is a flow chart for showing a procedure of calibration according to the first embodiment; and FIG. 3 is a block diagram showing the second embodiment of the present invention.

DETAILED DESCRIPTION

Next, embodiments of the present invention will be explained with reference to the attached drawings. At first, the first embodiment of the present invention will be explained while referring to FIGS. 1 and 2.

In FIG. 1, a calibration device according to the first embodiment of the present invention is totally shown by a numeral character 100. The calibration device 100 is provided with: a measurement housing 1, a filling vessel 2, accommodated in the measurement housing 1, to the filling vessel 2 a high pressure fuel gas such as hydrogen gas being fed from outside of the measurement housing 1; a scale 3 for measuring the weight of the measurement housing 1; and a main body housing 20 for accommodating the measurement housing 1 and the scale 3. The filling vessel 2 is mounted on a bottom face of the measurement housing 1 through a pedestal 8.

The weights of the measurement housing 1 before and after filling a fuel gas such as hydrogen gas are measured by the scale 3, and the weight of the hydrogen gas fed to and filled in the filing vessel 2 is calculated from the difference between the both weights. Hereinafter, the explanation will be made when hydrogen gas is adopted as a fuel gas.

The measurement housing 1 accommodating the filling vessel 2 and so on, and the main body housing 20 accommodating the scale 3 have moving means 20A such as wheels on their lower face, and they can move to a position at a calibration where an apparatus to be calibrated such as a hydrogen filling apparatus is installed.

On a side face of the measurement housing 1 is mounted a receptacle 6 as a hydrogen reception port, and when hydrogen gas is fed to and filled in the filling vessel 2 in the measurement housing 1 from the hydrogen filling apparatus 40 to be calibrated, the receptacle 6 becomes the hydrogen reception port on the side of the measurement housing 1.

That is, the hydrogen filling apparatus 40 and the measurement housing 1 are connected by the coupling of the filling nozzle 41 and the receptacle 6, and hydrogen gas is fed from the hydrogen filling apparatus 40 to the filling vessel 2 in the measurement housing 1.

In the measurement housing 1, the receptacle 6 and the filling vessel 2 are connected by the filling gas supply pipe 7. The hydrogen gas fed from the receptacle 6 to the measurement housing 1 is fed to and filled in the filling vessel 2 through the filling gas supply pipe 7.

In addition, the numeral 2A indicates a filling gas intake portion of the filling vessel 2, and the numeral 9 shows a check valve for preventing backflow of the hydrogen gas fed on the side of the measurement housing 1.

On the side face of the measurement housing 1 is detachably mounted a dry gas pipe 4 for feeding a dry gas to the measurement housing 1. The dry gas is fed from a supply source not shown to the measurement housing 1 through the dry gas pipe 4, and the dry gas can be filled in the measurement housing 1. Here, as the dry gas can be utilized inert gas such as nitrogen, argon and helium, carbon dioxide, and dried air. As the dry gas can be adapted any gases that can be obtained at low cost; easily filled into or discharged from the measurement housings 1, 10 for a short period of time; and has a characteristic contributing to improvement of safety.

Further, on the outer face of the measurement housing 1 is detachably mounted a dew-point instrument 5. Therefore, based on measured results of the dew-point instrument 5, it becomes possible to properly perform humidity management in the measurement housing For example, when the dew-point temperature in the measurement housing 1 is a prescribed temperature, which is −20° C. for instance, that is a dew-point temperature that can be judged it is sufficiently dried in the measurement housing 1, and a fuel gas, for example, hydrogen gas that is cooled at −40° C., is fed, amount of dew condensing on the receptacle 6, the filling gas supply pipe 7, the filling vessel 2 and other parts becomes few, so that the amount hardly effects on the weight measurement.

Here, it is expected that decreasing the dew point to −40° C. or less for instance causes the amount of the condensing dew to become zero, but the difference between the amount at −40° C. or less and that at −20° C. or less is small. Therefore, it is realistic and economical that the dew-point temperature is set from −20° C. to −25° C. as a reference dew-point temperature that can be judged to be necessarily and sufficiently dried.

In the embodiment shown in the drawings, the dew-point instrument 5 is mounted outside of the measurement housing 1, but can be mounted inside of the measurement housing 1.

Further, a control device not shown for transmitting measured values by the dew-point instrument 5 via infrared communication to the hydrogen filling apparatus 40 can be arranged to the dew-point instrument 5, which can control, with a simple construction, the hydrogen filling apparatus 40 so as to start the filling when the dew-point temperature in the measurement housing 1 reaches the predetermined temperature.

On the upper face of the measurement housing 1 is mounted a gas outlet 13, which becomes an outlet for discharging air and other gases with moisture outside of the measurement housing 1 when the dry gas is filled therein.

Further, on the upper face of the measurement housing 1 is mounted the filling gas outlet 11, which is connected to the filling vessel 2 through a filling gas release pipe 12.

In case that the hydrogen gas is discharged from the filling vessel 2, the hydrogen gas discharged from the filling vessel 2 is discharged through the filling gas release pipe 12 from the filling gas outlet 11 outside of the measurement housing 1. Not shown in the drawings, the main body housing 20 includes a gas release mechanism also.

The filling gas supply pipe 7 is fixed to a bottom face portion of the measurement housing 1 by a supporting member 14. In addition, the filling gas release pipe 12 is fixed to an outer wall portion of the measurement housing 1 by a supporting member 15. As constructions with the supporting member 14 and the supporting member 15 respectively to fix the filling gas supply pipe 7 and the filling gas release pipe 12 to the measurement housing 1, various conventional constructions can be utilized.

The pedestal 8 on which the supporting members 14 and 15 and the filling vessel 2 are mounted is formed of a heat insulating material with low heat conductivity such as rubber and resin. The reason is since low temperature in the measurement housing 1 conducts through the supporting members 14 and 15, and the pedestal 8 to an outer face of the measurement housing 1, it should be prevented that dew condenses on the measurement housing 1 and an outer face of the scale 3 that contact with the atmosphere.

Here, the measurement housing 1 is semi-enclosed structure. "Semi-enclosed structure" means a structure realizing not perfectly sealed state, but nearly sealed state. With this, feeding the dry gas in the measurement housing 1 makes an inner part of the measurement housing 1 slightly pressurized, so that it is prevented that air with moisture enters into the measurement housing 1.

Next, a procedure of calibration using the calibration device 100 shown in FIG. 1 will be explained while referring to FIG. 2.

In the flowchart of calibration shown in FIG. 2, in the step S1, at first, a weight of the measurement housing 1 before the hydrogen gas is filled is measured by the scale 3 under a condition that the dry gas pipe 4 and the filling nozzle 41 are not connected.

Then, the dry gas pipe 4 and the filling nozzle 41 are connected, and air and other gases with moisture in the measurement housing 1 are discharged as a scavenging work, and the hydrogen gas is filled from the hydrogen filling apparatus 40 to be calibrated to the filling vessel 2 as a filling work, and the dry gas pipe 4 and the filling nozzle 41 are disconnected as a disconnecting work.

Describing in detail, as the connecting work in the step S1, the dry gas pipe 4 is connected to one side face of the measurement housing 1. And, the filling nozzle 41 of the hydrogen filling apparatus 40 is connected to the receptacle 6 mounted on the side face of the measurement housing 1.

In the scavenging work, the dry gas is fed to and filled in the measurement housing 1 from a dry gas supply source not shown through the dry gas pipe 4. Filling the dry gas in the measurement housing 1 allows gases with moisture such as air existing in the measurement housing 1 to be discharged through the gas outlet 13 outside of the measurement housing 1.

The scavenging work is performed while monitoring the measured value by the dew-point instrument 5 at any time. As the scavenging proceeds, the dew-point temperature gradually decreases and humidity in the measurement housing 1 decreases. When the dew-point temperature reaches predetermined temperature such as −20° C., it is judged that it is sufficiently dried in the measurement housing 1.

Under the condition that the dew-point temperature reaches the predetermined temperature such as −20° C., it is sufficiently dried in the measurement housing 1, so that even if the hydrogen gas, which has been cooled at −40° C. is filled in the filling vessel 2 in the measurement housing 1, amount of dew condensing on the filling vessel 2, the receptacle 6, the filling gas supply pipe 7 and other parts is few, and the amount hardly effects on the weight measurement.

Here, it is expected that decreasing the dew point to −40° C. or less for instance causes the amount of the condensing dew to become zero, but the difference between the amount at −40° C. or less and that at −20° C. or less is small. Therefore, it is realistic and economical that the dew-point temperature is set from −20° C. to −25° C. as a reference dew-point temperature that can be judged to be necessarily and sufficiently dried.

By the scavenging work in the step S1, as described above, in case that the dew-point temperature reaches the predetermined temperature, and it can be judged that it is sufficiently dried in the measurement housing 1, the filling work in the step S1 is performed.

The filling hydrogen gas is performed until a pressure gauge (not shown) of the hydrogen filling apparatus 40 judges that a predetermined amount of hydrogen gas is fed.

After the filling work is finished, the disconnecting work in the step S1 is performed.

In the disconnecting work, the dry gas pipe 4 and the filling nozzle 41 are disconnected. Disconnecting the dry gas pipe 4 from the measurement housing 1, allows, at the weight measurement (in step S2) by the scale 3 as the calibration, influence of stresses generated in members configuring the dry gas pipe 4 to be removed from the measurement by the scale 3, which prevents that results of the weight measurements vary due to the stresses. When the step S1 is finished, the procedure moves to the step S2.

In the step S2, a weight that the hydrogen gas is filled from the hydrogen filling apparatus 40 to the filling vessel 2 in the measurement housing 1 (a weight of the measurement housing 1 after the hydrogen gas is filled) is measured by the scale 3. At the measurement after the hydrogen gas is filled, dew does not condense on the parts such as the filling vessel 2 in the measurement housing 1, so that accurate weight from which errors due to dew condensation are removed can be measured.

Then, measured results of the weights of the measurement housing 1 before and after the hydrogen gas is filled, the weight of the hydrogen gas filled in the filling vessel 2 is calculated to calculate the filling amount of the hydrogen gas. And, the calculated filling amount is compared to filling amount determined based on the flow meter of the hydrogen filling apparatus 40 to be calibrated, which performs a calibration of the hydrogen filling apparatus 40. When the step S2 is finished, the procedure moves to the step S3.

In the step S3 are displayed the weight value of the hydrogen gas that is the measured result in the step S2, the filling amount of the hydrogen gas calculated based on the weights of the measurement housing 1 before and after the filling, and the calibration result, to a display and so on not shown.

Further, the filling amount of the hydrogen gas that is the measured result, or the weight of the filled hydrogen gas is stored to a memorizing device of an information processor such as a PC (not shown) together with an identification number such as a product number of the hydrogen filling apparatus 40 to be calibrated, and day and time performing the calibration. Then, the calibration procedure is finished.

Not shown in FIG. 2 clearly, but, in case that the calibrations for other object apparatus are continuously performed by the calibration device 100, after the step S3, the hydrogen gas filled in the filling vessel 2 is discharged outside of the measurement housing 1 through the filling gas release pipe 12 and the filling gas discharging port 11.

In case that the calibrations for other hydrogen filling apparatus 40 are continuously performed, the procedure returns to "START" in FIG. 2, and works in the steps S1-S3 are performed.

Further, discharging of the hydrogen gas filled in the filling vessel 2 can be performed while the scale has been reset in the step S1 of the calibration for next object apparatus.

In the first embodiment shown in the drawings, the dry gas is filled in the measurement housing 1 through the dry gas pipe 4, and gases with moisture such as air are discharged outside of the measurement housing 1.

As a result, even when a fuel gas such as hydrogen gas, which has been cooled at −40° C., is fed to the filling vessel 2 in the calibration device 100, it is prevented that dew condenses on the equipment in the measurement housing 1, and the calibration with high accuracy, reliability and safety can be performed.

In addition, in the first embodiment, the dry gas pipe 4 is detachably mounted to the measurement housing 1, so that at the weight measurements in the calibration, the dry gas pipe 4 is separated from the measurement housing 1 to prevent that stresses generating in the members configuring the dry gas pipe 4 vary the results of the weight measurement.

At the weight measurements of the measurement housing 1, the dew-point instrument 5 can be separated.

In addition, in the first embodiment, since the measurement housing 1 is semi-enclosed structure, making the measurement housing 1 slightly pressurized by the dry gas can prevent air with moisture from entering into the measurement housing 1.

Therefore, even when the hydrogen, which has been cooled at −40° C., is filled in the filling vessel 2, it is prevented that dew condenses on the filling vessel 2, the receptacle 6, the filling gas supply pipe 7 and other parts.

Further, in the first embodiment is mounted the dew-point instrument 5 for measuring the dew-point temperature in the measurement housing 1, so that based on the measured results by the dew-point instrument 5, humidity management can be properly performed in the measurement housing 1.

For example, when the dew-point instrument 5 measures that the dew-point temperature reaches the predetermined temperature, for instance −20° C., which is a dew-point temperature that can be judged it is sufficiently dried in the measurement housing 1, it can be judged it is sufficiently dried in the measurement housing 1, and the hydrogen gas at −40° C. for instance may be filled in the measurement housing 1. Since it is sufficiently dried in the measurement housing 1 in such a case, amount of dew condensing on the filling vessel 2, the receptacle 6, the filling gas supply pipe 7 and other parts is few, and the amount hardly effects on the weight measurement.

Here, it is expected that decreasing the dew point to −40° C. or less for instance causes the amount of the condensing dew to become zero, but the difference between the amount at −40° C. or less and that at −20° C. or less is small. Therefore, it is realistic and economical that the dew-point temperature is set from −20° C. to −25° C. as a reference dew-point temperature that can be judged to be necessarily and sufficiently dried.

The first embodiment assumes to continuously perform the calibrations to plural hydrogen filling apparatuses 40.

When the calibration is performed only once, even when by filling the hydrogen gas, which has been cooled at −40° C. for instance in the filling vessel 2, dew condenses on the filling vessel 2, the receptacle 6, the filling gas supply pipe 7, and other parts, the weight of the measurement housing 1 is measured to perform accurate calibration after dew is sufficiently dried. But, in case that with a single calibration device 100 are continuously performed the calibrations to plural hydrogen filling apparatus 40, condensing dew on the filling vessel 2 causes the weight measurement to be suspended until the dew is sufficiently dried, so that it requires a long period of time to perform the calibrations.

In contrast, with the first embodiment, it is prevented that dew condenses on the equipment and pipes in the measurement housing 1, so that it is unnecessary to suspend the weight measurement until dew-condensed equipment and pipes are dried. Therefore, in case that plural hydrogen filling apparatus 40 are continuously calibrated by the calibration device 100, it is unnecessary to wait for drying of the equipment and the dew-condensed pipes every calibration, and it is possible to continuously fill in order to perform the calibrations and various tests.

Next, the second embodiment of the present invention will be explained while referring to FIG. 3.

In FIG. 3, a calibration device according to the second embodiment of the present invention is totally shown by the numeral character 200. The calibration device 200 is two-chamber structure in such a manner that the measurement housing 10 is divided into the first chamber 10A as a main chamber and the second chamber 10B as a subsidiary chamber, and the receptacle 6 as the hydrogen reception port from the hydrogen filling apparatus 40 to be calibrated is accommodated in the subsidiary chamber 10B.

Except that the subsidiary chamber 10B is installed in the measurement housing 10, and the receptacle 6 is accommodated in the subsidiary chamber 10B, the calibration device 200 according to the second embodiment has the same constructions as the calibration device 100 according to the first embodiment.

The calibration device 200 is provided with the measurement housing 10 having the main chamber 10A and the subsidiary chamber 10B, the filling vessel 2, accommodated in the main chamber 10A of the measurement housing 10, to which fuel gas such as hydrogen gas is fed from the outside of the measurement housing 10, the scale 3 for measuring the weight of the measurement housing 10, and a main body housing 30 for housing the measurement housing 10 with the main chamber 10A and the subsidiary chamber 10B, and the scale 3. The filling vessel 2 is mounted on the bottom face of the measurement housing 10A through the pedestal 8.

When the weight of the hydrogen gas fed to and filled in the filling vessel 2 is measured, in the same manner as the first embodiment, the weights of the measurement housing 10 before and after the hydrogen gas is filled are measured by the scale 3, and based on the weights of the measurement housing 10 before and after filling, filling amount of the hydrogen gas is calculated.

In the measurement housing 10, to the main chamber 10A are accommodated the filling vessel 2, the filling gas supply pipe 7, the filling gas release pipe 12 and the like, and the dry gas pipe 4 and the dew-point instrument 5 are disposed on the side face of the measurement housing 10. Positions and functions of the equipment in the main chamber A are, other than the receptacle 6, the same as those of the measurement housing 1 according to the first embodiment.

On the side face of the main chamber 10A on the side that the hydrogen gas is filled to the main chamber 10A, which is the right side face in FIG. 3, the subsidiary chamber 10B is disposed adjacent to the main chamber 10A, in the subsidiary chamber 10B is accommodated the receptacle 6, and the receptacle 6 is fixed to the subsidiary chamber 10B with a conventional condition not shown. In addition, to the receptacle 6 is connected one end of the filling gas supply pipe 7 whose other end is connected to the filling vessel 2 in the main chamber 10A. Numeral 9 indicates a check valve.

The border between the main chamber 10A and the subsidiary chamber 10B is isolated by side walls of the main chamber 10A and the subsidiary chamber 10B, and the filling gas supply pipe 7 penetrates the side walls to connect the filling vessel 2 with the receptacle 6.

In addition, on the portion that the filling gas supply pipe 7 penetrates the side walls of the main chamber 10A and the subsidiary chamber 10B, a sealing member 16 is mounted, the sealing member 16 prevents a gas with moisture such as air from communicating, through the through hole portion, between the main chamber 10A and the subsidiary chamber 10B.

In the subsidiary chamber 10B shown in FIG. 3, on the side face on the side that the hydrogen filling apparatus 40 to be calibrated is connected, which is the right side face in FIG. 3, a dry gas pipe 4A on the side of the subsidiary chamber for feeding dry gas in the subsidiary chamber 10B is detachably mounted. The dry gas is fed from a supply source not shown to the subsidiary chamber 10B through the dry gas pipe 4A, and can be filled in the subsidiary chamber 10B.

As the dry gas, as same as the first embodiment, can be utilized inert gas such as nitrogen, argon and helium, carbon dioxide and dried air.

When the hydrogen gas is filled, the filling nozzle 41 of the hydrogen filling apparatus 40 is coupled with the receptacle 6 in the subsidiary chamber 10B, and the hydrogen gas is fed from the hydrogen filling apparatus 40 on the side of the measurement housing 10.

Then, on the side face of the subsidiary chamber 10B on the side that the hydrogen filling apparatus 40 is connected to the subsidiary chamber 10B, which is the right side face in FIG. 3, a cover portion 10C that is openable/closeable with a pivot shaft 10D is mounted. Further, at a lower edge of the side cover portion 10C and a portion opposing the lower edge thereof on the subsidiary chamber 10B side are mounted cover portion sealing members 10E, 10F separately configuring a flexible member with continuous cell structure such as sponge are mounted, on a side edge of the cover portion 10C also is mounted a sealing member not shown.

In order to couple the filling nozzle 41 with the receptacle 6, the cover portion 10C is opened to insert the filling nozzle 41 into the subsidiary chamber 10B. After the coupling, the cover portion 10C is closed to perform filling hydrogen.

When the hydrogen gas is filled, the hydrogen pipe 42 of the hydrogen filling apparatus 40 is caught by the cover portion sealing members 10E, 10F, and the caught portions of the hydrogen pipe 42 are sealed.

But under the condition that the hydrogen pipe 42 is caught by the cover portion sealing members 10E, 10F, it is not sufficiently sealed, and there is a possibility that the dry gas in the subsidiary chamber 10B leaks outside.

Then, in the calibration device 200 according to the second embodiment, it is set that flow rate as circulation amount of the dry gas per unit volume in the subsidiary chamber 10B is more than that in the main chamber 10A. For example, it is preferable that the circulation flow rate of the dry gas in the subsidiary chamber 10B is multiples of that in the main chamber 10A, and the circulation flow rates can be separately adjusted. Circulating large amount of dry gas into the subsidiary chamber 10B prevents air with moisture from entering into the subsidiary chamber 10B through a portion that the hydrogen pipe 42 is caught by the cover portion sealing members 10E, 10F.

The calibration procedure with the calibration device 200 shown in FIG. 3 is basically the same as that of the calibration device 100 according to the first embodiment explained while referring to FIG. 2. But, in the calibration with the calibration device 200, a connecting work of the dry gas pipe 4A, a work scavenging the subsidiary chamber 10B through the dry gas pipe 4A, and a detaching work of the dry gas pipe 4A are further performed in the step S1 shown in FIG. 2.

In the second embodiment shown in FIG. 3, the dew-point instrument 5 is mounted in the main chamber 10A, and not mounted in the subsidiary chamber 10B, and humidity management in the main chamber 10A is performed. With this, start of hydrogen filling is judged based on the measured results by the dew-point instrument 5. But, it is possible that a dew-point instrument not shown is mounted in the subsidiary chamber 10B also to judge a timing that filling hydrogen starts based on the both of the measured results of the dew-point instrument 5 of the main chamber 10A and the dew-point instrument of the subsidiary chamber 10B.

With the second embodiment, the measurement housing 10 has the main chamber 10A accommodating the filling vessel 2, and the subsidiary chamber 10B accommodating the receptacle 6, and the filling nozzle 41 and the hydrogen pipe 42 at filling hydrogen, so that dew slightly condenses on the equipment accommodated in the subsidiary chamber 10B only when the filling nozzle 41 is detached from the receptacle 6 and at filling, and it can be prevented that dew condenses on the equipment accommodated in the main chamber 10A. Therefore, amount of dew condensing in overall calibration device 200 decreases.

Here, amounts of dews condensing on the receptacle 6, the filling nozzle 41, the hydrogen pipe 42 and the like are large, and surface areas of the receptacle 6, the filling nozzle 41, and the hydrogen pipe 42 are small in comparison with those of the equipment accommodated in the main chamber 10A, so that even when dew condenses in the subsidiary chamber 10B, it has little effect on the weight measurements by the scale 3. Then, accommodating the receptacle 6, the filling nozzle 41, and the hydrogen pipe 42 in the subsidiary chamber 10B apart from the main chamber 10A can greatly suppress degradation of measuring accuracy.

In addition, there is a possibility that into the second chamber 10B enters air with moisture every time the filling nozzle 41 is detached from the receptacle 6, and into the subsidiary chamber 10B enters the air with moisture through the cover portion sealing members 10E, 10F such as sponges of the cover portion 10C at every filling. But, in the second embodiment, flow rate of the dry gas per unit volume in the second chamber 10B is more than that in the first chamber 10A, which prevents the air with moisture from entering into the subsidiary chamber 10B. And, a possibility that the air with moisture enters into the main chamber 10A can be further decreased.

In the second embodiment shown in FIG. 3, constructions and effects other than those described above are the same as those of the first embodiment explained with reference to FIGS. 1 and 2.

The embodiments shown in drawings are just examples, and a technical field of the present invention is not limited to the embodiments. For example, in the embodiments shown in the drawings, a calibration device for a hydrogen filling apparatus is explained, but, the present invention is applicable to a calibration device for a CNG filling apparatus.

DESCRIPTION OF THE REFERENCE NUMERALS 1, 10 measurement housings
2 filling vessel
3 scale
4, 4A dry gas pipes
5 dew-point instrument
6 receptacle (hydrogen gas inlet)
7 filling gas supply pipe
8 pedestal
9 check valve
10A first chamber of measurement housing (main chamber)
10B second chamber of measurement housing (subsidiary chamber)
10C cover portion
10D pivot shaft
10E, 10F cover portion sealing members (sponges and others)
11 filling gas outlet
12 filling gas release pipe
13 gas outlet
14, 15 supporting members
16 sealing member
20, 30 main body housings
20A, 30A moving means (wheels and others)
40 hydrogen filling apparatus
41 filling nozzle
42 hydrogen pipe
100, 200 calibration devices

What is claimed is:

1. A calibration device comprising:
a filling vessel, accommodated in a measurement housing, to said filling vessel a high pressure fuel gas being fed from outside of the measurement housing;
a dew-point instrument for measuring a dew-point temperature in the measurement housing; and
a scale for measuring a weight of a fuel gas fed to the filling vessel,
wherein a dry gas pipe for feeding a dry gas in the measurement housing is detachably mounted to the measurement housing.

2. The calibration device as claimed in claim 1, wherein said measurement housing is semi-enclosed structure.

3. The calibration device as claimed in claim 2, wherein said measurement housing comprising a first chamber with the filling vessel and a second chamber for accommodating a receptacle.

4. The calibration device as claimed in claim 1, wherein said measurement housing comprising a first chamber with the filling vessel and a second chamber for accommodating a receptacle.

5. The calibration device as claimed in claim 1, further comprising a filling gas supply pipe in fluid communication with the filling vessel to facilitate filling of the filling vessel with gas.

6. The calibration device as claimed in claim 5, further comprising a filling gas release pipe in fluid communication with the filling vessel to facilitate discharge of gas from the filling vessel.

7. The calibration device as claimed in claim 1, further comprising a gas outlet mounted on the measurement housing for discharging gas from the measurement housing.

* * * * *